United States Patent
Ohara et al.

(10) Patent No.: US 8,986,194 B2
(45) Date of Patent: Mar. 24, 2015

(54) ENDOSCOPE APPARATUS

(71) Applicant: Olympus Corporation, Tokyo (JP)

(72) Inventors: Jin Ohara, Hachioji (JP); Shinji Yasunaga, Higashimurayama (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/905,252

(22) Filed: May 30, 2013

(65) Prior Publication Data

US 2013/0261395 A1 Oct. 3, 2013

Related U.S. Application Data

(63) Continuation of application No. PCT/JP2011/078089, filed on Dec. 5, 2011.

(30) Foreign Application Priority Data

Dec. 7, 2010 (JP) .................................. 2010-272892

(51) Int. Cl.
| | |
|---|---|
| A61B 1/00 | (2006.01) |
| A61B 1/12 | (2006.01) |
| G02B 7/00 | (2006.01) |
| G02B 23/24 | (2006.01) |
| A61B 1/04 | (2006.01) |

(52) U.S. Cl.
CPC .................. *A61B 1/12* (2013.01); *A61B 1/0008* (2013.01); *A61B 1/128* (2013.01); *A61B 1/125* (2013.01); *G02B 7/008* (2013.01); *G02B 23/2492* (2013.01)
USPC .......................................... 600/101; 600/152

(58) Field of Classification Search
CPC .............................. A61B 1/125; A61B 1/128
USPC ............ 600/127, 129, 141, 169, 152; 165/97; 417/96–98, 103, 122, 217, 473; 348/65
See application file for complete search history.

(56) References Cited

U.S. PATENT DOCUMENTS

2009/0315986 A1 12/2009 Ohara

FOREIGN PATENT DOCUMENTS

| JP | 05092007 A | * 4/1993 | ............ A61B 17/22 |
|---|---|---|---|
| JP | 09-090243 A | 4/1997 | |
| JP | 2007-007397 A | 1/2007 | |
| JP | 2010-022815 A | 2/2010 | |

OTHER PUBLICATIONS

Machine Translation of Japanese Patent 05-092007 to Karasawa, 8 pages.*
International Search Report dated Jan. 10, 2012 issued in PCT/JP2011/078089.
International Preliminary Report on Patentability together with the Written Opinion dated Jun. 20, 2013 received in related International Application No. PCT/JP2011/078089.

* cited by examiner

*Primary Examiner* — Anhtuan T Nguyen
*Assistant Examiner* — Timothy J Neal
(74) *Attorney, Agent, or Firm* — Scully, Scott, Murphy & Presser, PC (57) ABSTRACT

The endoscope apparatus includes a heat exchanger, a first tube, and a second tube. The front-end portion is cooled down by repeating alternately, the other operation which is opposite an one operation, which is an operation of generating a flow of the cooling liquid from the other end of the first tube to the one end of the first tube, and a flow of the cooling liquid from the one end of the second tube to the other end of the second tube, and the one operation which is an operation of generating a flow of the cooling liquid from the other end of the second tube to the one end of the second tube, and a flow of the cooling liquid from the one end of the first tube to the other end of the first tube.

6 Claims, 6 Drawing Sheets

ENDOSCOPE APPARATUS

CROSS-REFERENCE TO RELATED APPLICATION

"The present application is based upon and claims the benefit of priority from the prior Japanese Patent Application No. 2010-272892 filed on Dec. 7, 2010; the entire contents of which are incorporated herein by reference."

BACKGROUND OF THE INVENTION

1. Field of the Invention

The present invention relates to a technology for cooling an endoscope apparatus.

2. Description of the Related Art

Among endoscope apparatuses (systems), there are apparatuses hitherto known, in which, a drive actuator (such as an electric drive actuator in which, a shape memory alloy has been used) for deforming a scope section as desired, and other electronic components (such as a light emitting diode) are built-in in a flexible, long and slender scope section which is to be inserted into an abdominal cavity.

Since the drive actuator and the electronic components generate heat, for suppressing an effect on a human body or for suppressing overheating of electronic equipment, there are supposed to be cases in which, cooling down becomes necessary.

For the abovementioned reason, in Patent Document 1 for example, a cooling circuit of an endoscope system has been proposed.

Figure 6:
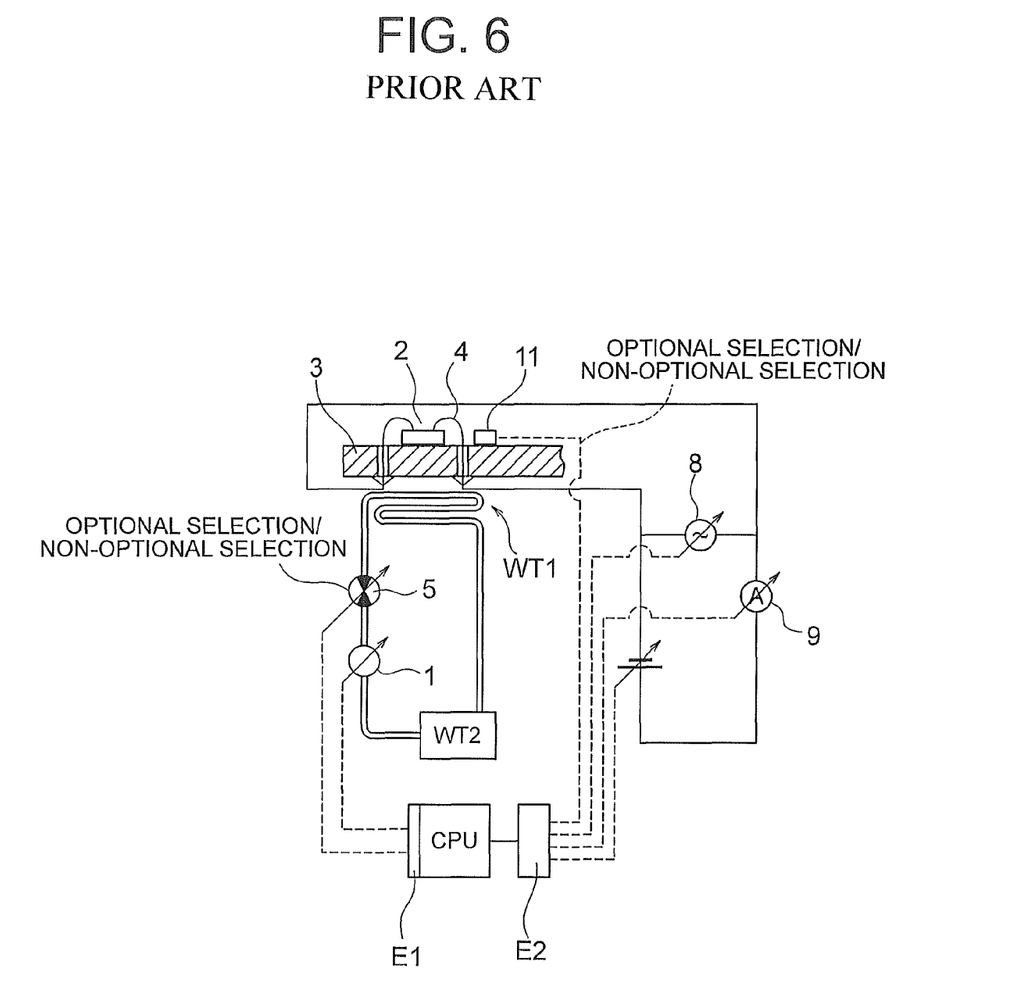
FIG. 6 is a diagram showing an example of a cooling circuit of a conventional endoscope system.

The cooling circuit, as shown in FIG. 6, includes a supply pump 1 for feeding a cooling medium, a first heat exchanger WT1 which is fluid-connected to the supply pump upon passing through a supply passage, and a second heat exchanger WT2 which is fluid-connected to the first heat exchanger WT1 and the supply pump 1 (closed circuit).

CITATION LIST

Patent Literature

Patent Document 1: Japanese Patent Application Laid-open Publication No. 2007-7397

SUMMARY OF THE INVENTION

However, in a case in which, an attempt is made to install the entire cooling circuit described in Patent Document 1, at an interior of a long and slender scope section of the endoscope system, since the supply pump 1 in the closed circuit needs a large space in an extreme radial direction (a direction orthogonal to a longitudinal direction of the long and slender scope section), this portion is to be installed in an operating section (refer to reference numeral 140 in FIG. 1 for example) for operating a displacement etc. of the scope section.

In this case, a distance from the first heat exchanger WT1 which is disposed at a front-end portion of the scope section, up to the supply pump 1 reaches up to one meter or more.

Consequently, the supply pump 1 is required to circulate a cooling liquid by a small-diameter tube of a length two meters or more both way (since the tube is disposed in a shaft portion of the endoscope (refer to reference numeral 141a in FIG. 2 for example), it is not possible to use a large-diameter tube due to a constraint on space).

Therefore, the supply pump 1 is sought to have a sufficient liquid sending capacity as well as a high discharge pressure.

However, disposing such pump having a high performance leads to an increase in size and an increase in weight, which consequently leads to an increase in electric power consumption, and noise and vibration. Therefore, there is a possibility of an adverse effect on operability and economic efficiency.

The present invention has been made in view of the abovementioned circumstances, and an object of the present invention is to provide a cooling system of an endoscope apparatus, which, while having a simple, light-weight, compact, and low-cost structure, enables to cool down favorably heat generating components which are provided at a front-end portion etc. of the endoscope, and furthermore, to provide the endoscope apparatus.

To solve the abovementioned issues and to achieve the object, an endoscope apparatus according to the present invention having a scope section which includes at least a front-end portion and a shaft portion, includes a heat exchanger which is installed near a front end, and which has a channel for a cooling liquid for cooling a functional component disposed in the front-end portion, which generates heat, a first tube of which, one end is connected to one end of the channel of the heat exchanger, and which is extended toward the shaft portion, and a second tube of which, one end is connected to the other end of the channel of the heat exchanger, and which is extended toward the shaft portion, and the front-end portion is cooled down by repeating alternately, the other operation which is opposite an one operation, further which is an operation of generating a flow of the cooling liquid from the other end of the first tube to the one end of the first tube, and a flow of the cooling liquid from the one end of the second tube to the other end of the second tube, and the one operation which is an operation of generating a flow of the cooling liquid from the other end of the second tube to the one end of the second tube, and a flow of the cooling liquid from the one end of the first tube to the other end of the first tube.

The endoscope apparatus according to the present invention includes a first reservoir which is capable of holding a predetermined amount of the cooling liquid at the other end of the first tube, and a second reservoir which is capable of holding a predetermined amount of the cooling liquid at the other end of the second tube, and a displacement mechanism which is capable of advancing and retreating is fitted by a pressurized contact with the first reservoir, and the other operation which is opposite the one operation, and the one operation are caused by the advance and the retreat of the displacement mechanism.

According to the present invention, it is possible to provide a cooling system of an endoscope apparatus, which, while having a simple, light-weight, compact, and low-cost structure, enables to cool down favorably heat generating components which are provided at a front-end portion of the endoscope, and furthermore, to provide the endoscope apparatus.

DETAILED DESCRIPTION OF THE INVENTION

An exemplary embodiment of an endoscope apparatus according to the present invention will be described below in detail by referring to the accompanying diagrams. However, the present invention is not restricted to the embodiment described below.

First Embodiment

Figure 1:
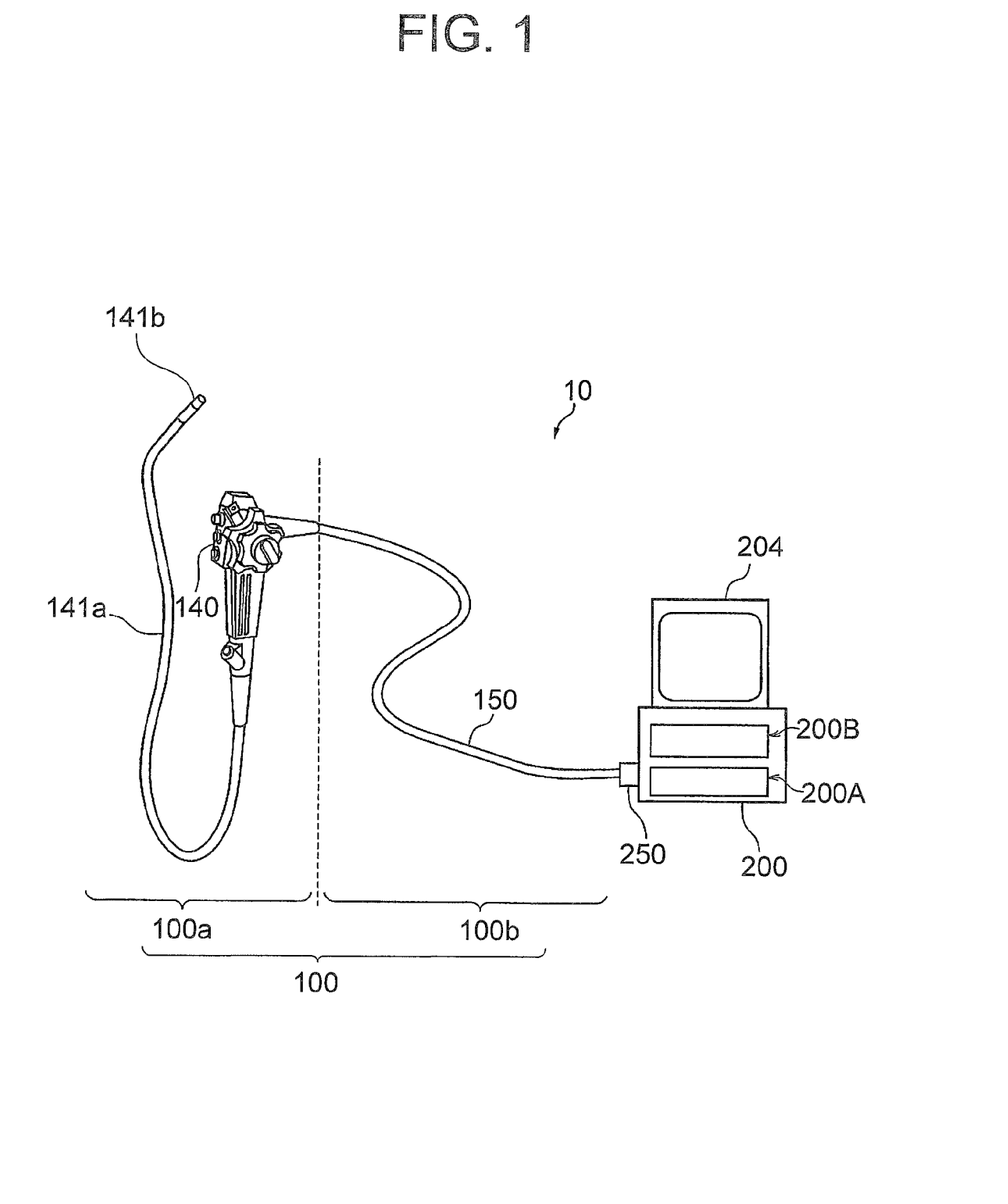
FIG. 1 is a diagram showing a schematic arrangement of an electronic endoscope system according to a first embodiment of the present invention.

FIG. 1 is a diagram showing a schematic arrangement of an electronic endoscope system 10 according to a first embodiment of the present invention. The electronic endoscope system 10 includes an electronic endoscope (endoscope apparatus) 100 and an apparatus outside the body 200.

The electronic endoscope 100 includes a scope section 100a and a connecting-cord section 100b. Moreover, the apparatus outside the body 200 includes a power supply unit 200A, a video processor 200B which carries out processing of a video signal from the electronic endoscope 100, and a display unit 204 which displays on a monitor the video signal from the video processor 200B. The scope section 100a corresponds to an apparatus inside the body.

The scope section 100a is divided mainly into an operating section 140 and an inserting section 141.

Figure 2:
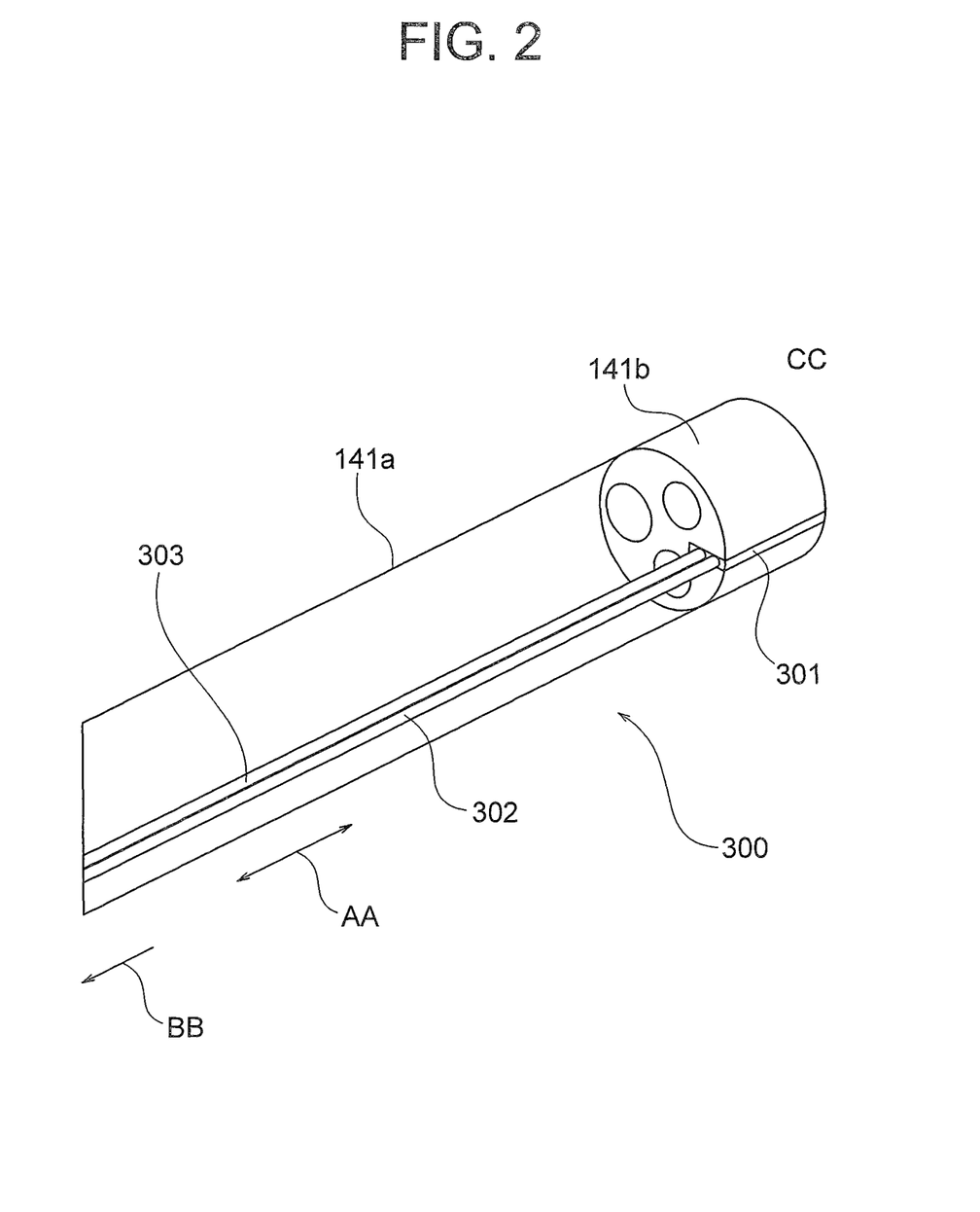
FIG. 2 is an enlarged perspective view showing in an enlarged form, a vicinity of a front-end portion of an endoscope in the electronic endoscope system according to the first embodiment.

The inserting section 141 includes a long and slender member (a shaft portion 141a) having a flexibility which can be inserted into an abdominal cavity of a patient and a rigid portion (a front-end portion) 141b at a front end (refer to FIG. 2). A user is capable of carrying out various operations by an angle knob which has been provided to the operating section 140.

The connecting-cord section 100b is extended from the operating section 140. The connecting-cord section 100b includes a universal cord 150. The universal cord 150 is connected to the apparatus outside the body 200 via a connector 250.

Moreover, the universal cord 150 communicates a power-supply voltage signal and a CCD (charge coupled device) drive signal from the power supply unit 200A and the video processor 200B, to the scope section 100a, as well as communicates a video signal from the scope section 100a to the video processor 200B. Peripheral equipment such as a VTR (video tape recorder) deck and a video printer which are not shown in the diagram, are connectable to the video processor 200B in the apparatus outside the body 200. The video processor 200B is capable of carrying out a predetermined signal processing on a video signal from the scope section 100a, and displaying an endoscope image on a display screen of the display unit 204.

Here, the inserting section 141 of the scope section 100a of the electronic endoscope apparatus 100 according to the first embodiment includes the shaft portion 141a which is flexible, and the rigid portion (a front-end metallic member) 141b.

Functional elements such as a light guide and an LED (light emitting diode) which become a light source, and an image pickup unit are assembled in the rigid portion 141b.

Moreover, as shown in FIG. 2, there is a notch in a peripheral portion of the rigid portion 141b, and a water-cooling jacket 301 (of about 8 mm length in a longitudinal direction AA, 1.2 mm width, and 0.6 mm thickness typically) having a U-shaped channel which is bent at a front-end side CC, is joined to the notch.

Moreover, a first tube 302 and a second tube 303 which are flexible are connected to two ends respectively of the U-shaped channel of the water-cooling jacket 301. A non-volatile cooling medium is filled in the U-shaped channel of the water-cooling jacket 301, and in the first tube 302 and the second tube 303.

The water-cooling jacket 301, the first tube 302, the second tube 303, and the cooling medium etc. form a part of a cooling system 300 according to the first embodiment.

Here, when there is a flow of the cooling liquid, heat which is generated by the functional elements assembled in the rigid portion (front-end metallic member) 141b is transmitted through the rigid portion (front-end metallic member) 141b, and upon being transferred to the cooling medium via the water-cooling jacket 301, the heat is transferred to a base-end side BB (the base-end side BB in the longitudinal direction AA of the inserting section 141 (shaft portion 141a)).

Figure 3:
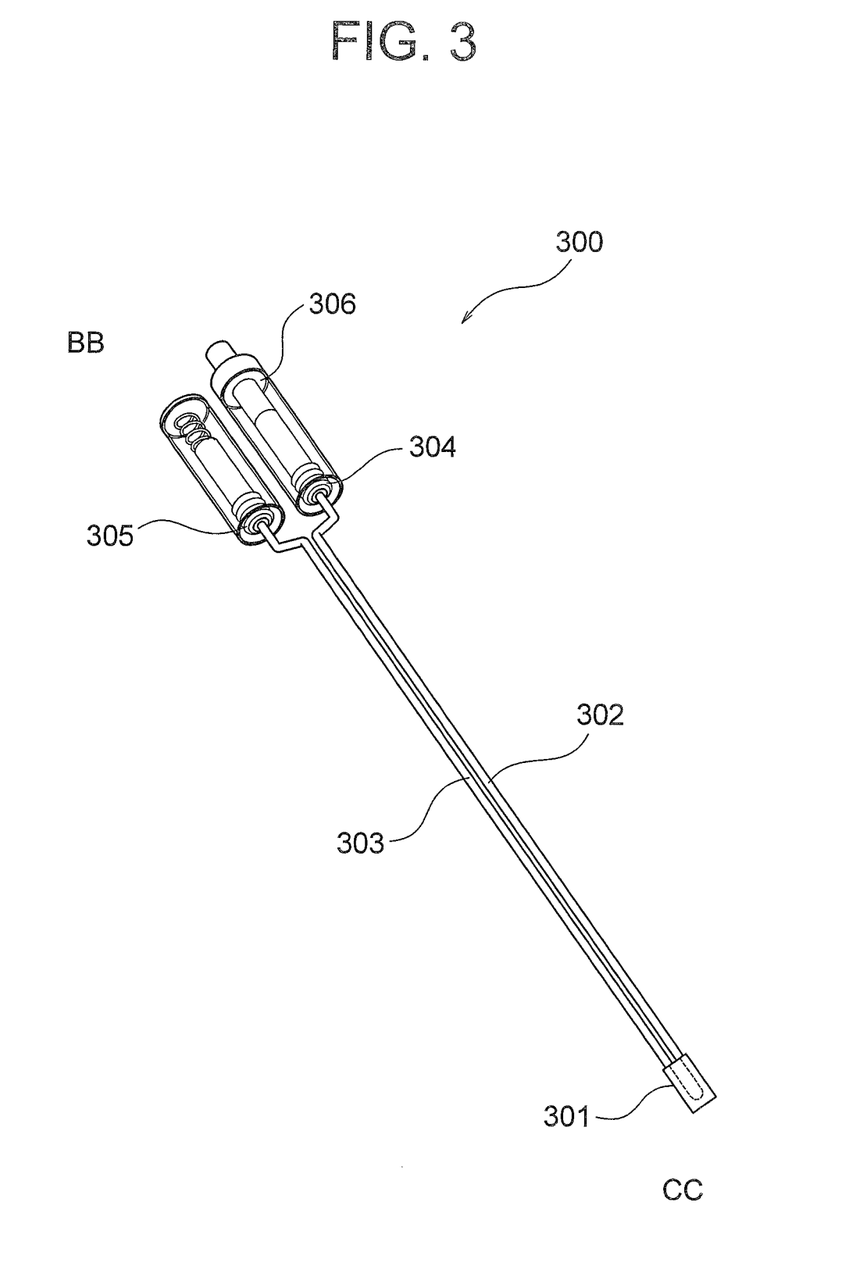
FIG. 3 is a perspective view showing an overall structure of a cooling system according to the first embodiment.

FIG. 3 shows an overall structure of the cooling system 300.

A base-end portion of the first tube 302 and a base-end portion of the second tube 303 which are connected to the water-cooling jacket 301 which functions as a heat exchanger are connected to a first reservoir 304 and a second reservoir 305 respectively. Each of the first reservoir 304 and the second reservoir 305 has a bellows structure which is contractible and expandable and a volume of the first reservoir 304 and a volume of the second reservoir 305 change by compressing or elongating in a longitudinal direction. Moreover, the cooling medium is filled also in the first reservoir 304 and the second reservoir 305.

Figure 4:
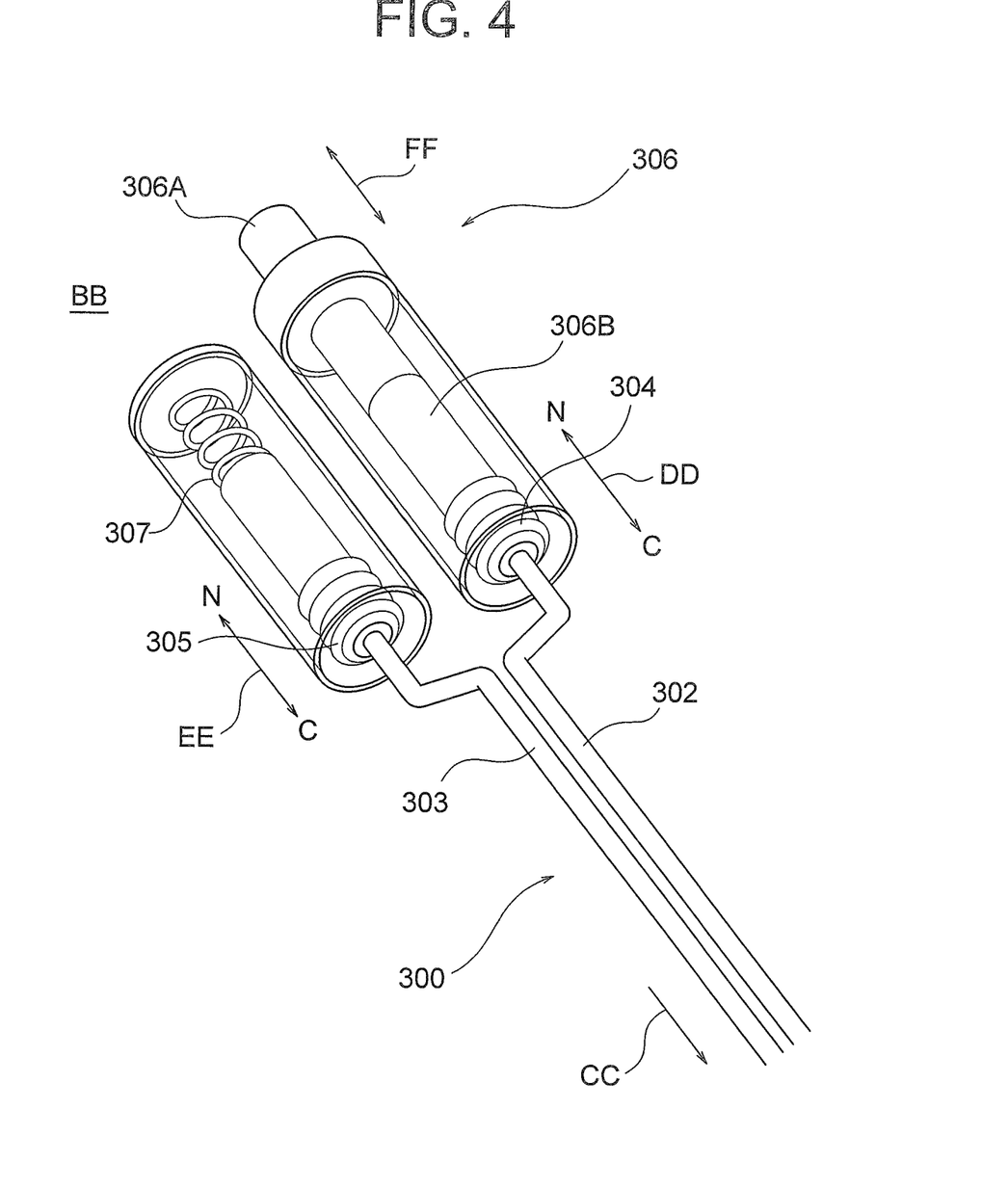
FIG. 4 is an enlarged perspective view showing in an enlarged form, a base-portion (an actuator structure) of the cooling system according to the first embodiment.

FIG. 4 is an enlarged view of a base-end portion of the cooling system 300.

A linear actuator 306 which is capable of advancing and retreating in the longitudinal direction is disposed on a base-end side BB of the first reservoir 304. An arrangement is made such that, with a displacement of a movable portion 306A of the linear actuator 306, it is possible to compress or to elongate the bellows structure of the first reservoir 304 via a pressurized-contact making member 306B.

A bias spring is disposed on a base-end side BB of the second reservoir 305. The cooling medium which has been filled in the U-shaped channel at an interior of the water-cooling jacket 301, the first tube 302, the second tube 303, the first reservoir 304, and the second reservoir 305 are incompressible. Therefore, when the first reservoir 304 is compressed, the second reservoir 305 is elongated, and when the second reservoir 305 is compressed, the first reservoir 304 is elongated.

In the diagram, an arrow DD indicates a direction of contraction and expansion of the first reservoir 304, reference numeral C indicates a direction of contraction, and reference numeral N indicates a direction of elongation. An arrow EE indicates a direction of contraction and expansion of the second reservoir 305, reference numeral C indicates a direction of contraction, and reference numeral N indicates a direction of elongation. An arrow FF indicates a direction of a reciprocating movement of the linear actuator 306.

FIG. 5A, FIG. 5B, FIG. 5C, and FIG. 5D are diagrams explaining a flow of the cooling medium of the cooling system 300.

Figure 5A:
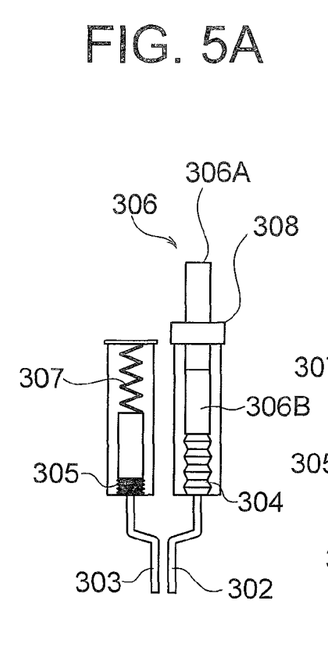
FIG. 5A, FIG. 5B, FIG. 5C, and FIG. 5D (hereinafter, 'FIG. 5A to FIG. 5B') are explanatory diagrams related to a flow of a cooling medium and operating conditions of a linear actuator in the cooling system according to the first embodiment.

FIG. 5A indicates a state in which, the movable portion 306A of the linear actuator 306 has displaced to an extreme base-end in the longitudinal direction (let to be an uppermost position in FIG. 5A, and a direction in FIG. 5A, FIG. 5B, FIG. 5C, and FIG. 5D for a direction here onward) of the inserting section 141 (shaft portion 141a). A position of a linear actuator fixed-portion 308 is fixed.

At this time, the second reservoir 305 is compressed by the bias spring 307, and as a result, the first reservoir 304 is elongated, thereby pushing the pressurized-contact making member 306B upward up to a position of making a pressurized contact with the movable portion 306A of the linear actuator 306.

Figures 5B, 5C:
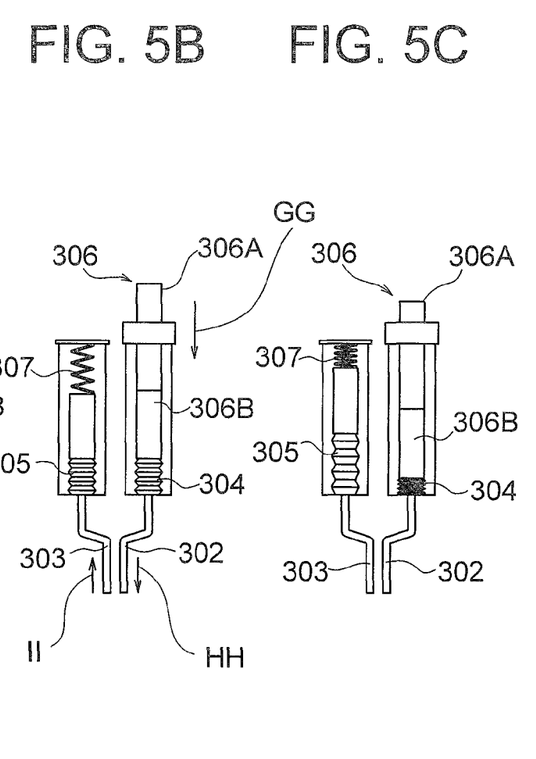

Next, as shown in FIG. 5B, as the movable portion 306A of the linear actuator 306 moves downward and compresses the first reservoir 304, in accordance with the compression of the first reservoir 304, the second reservoir 305 elongates, resisting the bias spring 307.

Figure 5D:
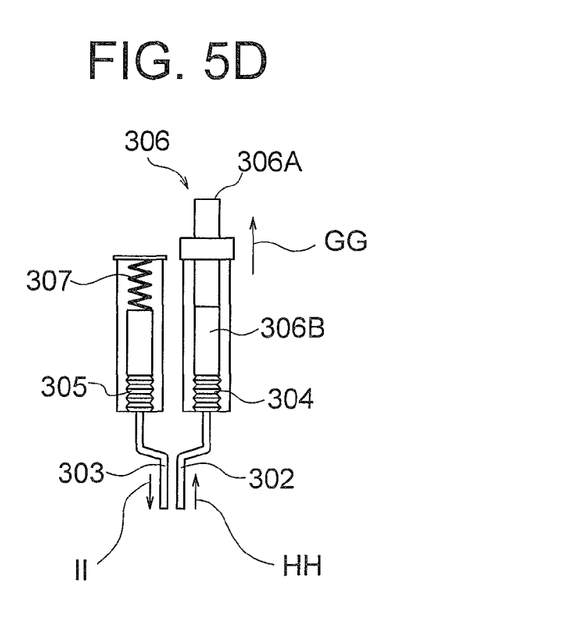

Here, in FIG. 5B and FIG. 5D, an arrow GG indicates a direction of movement of the linear actuator 306. An arrow HH indicates a direction of flow of the cooling liquid in the first tube 302. An arrow II indicates a direction of flow of the cooling liquid in the second tube 303.

At this time, a downward flow of the cooling medium is generated inside the first tube 302 and an upward flow of the cooling medium is generated inside the second tube 303.

Accordingly, a flow of the cooling medium is generated inside the U-shaped channel of the water-cooling jacket 301, and the rigid portion (front-end metallic member) 141b is cooled down.

FIG. 5C is a diagram showing a state in which, the movable portion 306A of the linear actuator 306 is displaced down to the lowermost position, after moving from the state in FIG. 5B. In FIG. 5C, the first reservoir 304 is compressed up to the lowermost position, and with the compression of the first reservoir 304, the second reservoir 305 assumes a state of being elongated up to the uppermost position.

Next, as shown in FIG. 5D, the movable portion 306A of the linear actuator 306 is moved upward (or a drive of the linear actuator 306 is disengaged).

At this time, the second reservoir 305 is compressed by the bias spring 307, and with the compression of the second reservoir 305, the pressurized-contact making member 306B of the first reservoir 304, which has been elongated is pushed upward up to a position of making a pressurized contact with the movable portion 306A of the linear actuator 306. At this time, a downward flow of the cooling medium is generated inside the second tube 303, and an upward flow of the cooling medium is generated inside the first tube 302 (in other words, a flow in a reverse direction of FIG. 5B).

Accordingly, a flow of the cooling medium is generated inside the U-shaped channel of the water-cooling jacket 301 which functions as a heat exchanger, and the rigid portion (front-end metallic member) 141b is cooled down.

Furthermore, as the movable portion 306a of the linear actuator 306 moves up to the uppermost position, a state same as the state in FIG. 5A is assumed.

In such manner, by repeating operations shown in FIG. 5A to FIG. 5D in order of FIG. 5A→FIG. 5B, FIG. 5C→FIG. 5D→FIG. 5A, by a reciprocating displacement of the linear actuator 306, it is possible to cool down the rigid portion (front-end metallic member) 141b continuously.

In a precise sense, the flow of the cooling medium stops in the state in FIG. 5A and FIG. 5C. However, this stopping of the flow is temporary, and no major problem arises for a cooling effect.

In such manner, in a method according to the first embodiment, since it is possible to achieve the cooling effect only by the reciprocating displacement of the movable portion 306A of the linear actuator 306, it is possible to build a cooling system which is smaller in size and lighter in weight as compared to a conventional cooling system in which, a circulating pump is used.

In the first embodiment, the displacement (movement) of the cooling medium inside the first tube 302 and the second tube 303, by the reciprocating movement, is a value obtained by multiplying a displacement of the linear actuator 306 by a ratio of a cross-sectional area of the first reservoir 304 and the second reservoir 305, and a cross-sectional area of the first tube 302 and the second tube 303.

For instance, in a case in which, an inner diameter of the first tube 302 (the second tube 303) is 0.3 mm, an average inner diameter of the first reservoir 304 (the second reservoir 305) is 3 mm, and an amount of displacement of the movable portion 306A of the linear actuator 306 is 5 mm, the displacement of the cooling medium inside the first tube 302 (the second tube 303) becomes 500 mm. Since the amount of displacement inside the first tube 302 (the second tube 303) which is necessary, varies according to a thermal conductivity and an amount of heat generated by the rigid portion (front-end portion) 141b, the optimum designing may be carried out according to the situation.

The cooling system 300 of the electronic endoscope system 10 according to the first embodiment has an arrangement of causing reciprocating movement without circulating the cooling liquid inside the tube as in a conventional cooling system, and the heat which is transferred to the cooling liquid from the rigid portion (front-end portion) 141b, and consequently from the water-cooling jacket (heat exchanger) 301, is released to the surrounding in a process of moving to the base-end side BB of the shaft portion 141a inside the first tube 302 and the second tube 303. Therefore, when it is possible to move the cooling liquid only by a predetermined distance (such as about 30 cm to 50 cm typically), it is possible to achieve a cooling capacity equivalent to a cooling capacity achieved in a case of circulating the cooling liquid. Since a linear actuator is sufficient for the reciprocating movement of the cooling liquid, a smaller size and a lighter weight as compared to a case of using a circulating pump is possible.

In such manner, according to the electronic endoscope system 10 which includes the cooling system 300 according to the first embodiment, since it is possible to achieve a favorable cooling effect only by the reciprocating displacement of the linear actuator, it is possible to provide the electronic endoscope system 10 which is smaller in size, lighter in weight, low-cost, and low-noise, as compared to a case of using a circulating pump as in the conventional technology.

The present invention is not restricted to the abovementioned first embodiment of the present invention, and various modifications and changes may be made without departing from the scope of the invention.

As it has heretofore been described, the present invention enables to cool down favorably components provided in a front-end portion of an endoscope, while having a simple, light-weight, compact, and low-cost structure, and is useful in a field related to an endoscope apparatus for instance.

REFERENCE SIGNS LIST 10 electronic endoscope system
100 electronic endoscope (corresponds to endoscope apparatus of the present invention)
100a scope section
100b connecting-cord section
140 operating section
141 inserting section
141a shaft portion
141b rigid portion (front-end metallic member: front-end portion)
200 apparatus outside the body
300 cooling system
301 water-cooling jacket (heat exchanger)
302 first tube
303 second tube
304 first reservoir (cooling-liquid accommodating container)
305 second reservoir (cooling-liquid accommodating container)
306 linear actuator (displacement mechanism)
306A movable portion
306B pressurized-contact making member

What is claimed is:

1. An endoscope apparatus having a scope section which includes at least a front-end portion and a shaft portion, the endoscope apparatus comprising:
a heat exchanger which is installed near the front-end portion, and which has a channel for a cooling liquid for cooling a functional component which generates heat, the functional component being disposed in the front-end portion;
a first tube having one end connected to one end of the channel of the heat exchanger;
a second tube having one end connected to an other end of the channel of the heat exchanger, and
an actuator in fluid communication with one of the first and second tubes and disposed so as to be reciprocated in a first and second direction,
wherein the front-end portion is cooled down by alternating reciprocations of the actuator in a repetitive manner to generate a first flow of the cooling liquid from the first tube through the heat exchanger to the second tube when the actuator is reciprocated in the first direction and to generate a second flow of the cooling liquid from the second tube through the heat exchanger to the first tube when the actuator is reciprocated in the second direction.

2. The endoscope apparatus according to claim 1, comprising:
a first reservoir which is capable of holding a predetermined amount of the cooling liquid at an other end of the first tube; and
a second reservoir which is capable of holding a predetermined amount of the cooling liquid at an other end of the second tube, wherein
the cooling fluid flows from the first reservoir into the second reservoir when the actuator is reciprocated in the first direction and the cooling fluid flows from the second reservoir into the first reservoir when the actuator is reciprocated in the second direction.

3. The endoscope apparatus according to claim 2, wherein the first and second reservoirs have a variable volume.

4. The endoscope apparatus according to claim 3, wherein the first and second reservoirs are bellows which can contract and expand in the first and second directions, respectively.

5. The endoscope apparatus according to claim 1, wherein the actuator is configured to reciprocate linearly between the first and second directions.

6. The endoscope apparatus according to claim 1, further comprising a biasing member for biasing the actuator in one of the first and second directions.

* * * * *